United States Patent [19]

Camiener

[11] Patent Number: 5,770,404

[45] Date of Patent: Jun. 23, 1998

[54] PREPARATION OF HEMOPROTEINS FROM APOPROTEINS AND HEME-LIKE PORPHYRINS DERIVED FROM CHLOROPHYLL

[76] Inventor: Gerald W. Camiener, P.O. Box 39370, Solon, Ohio 44139

[21] Appl. No.: 659,416

[22] Filed: Jun. 6, 1996

Related U.S. Application Data

[60] Provisional application No. 60/000,223 Jun. 14, 1995.

[51] Int. Cl.[6] .......................... C12P 21/04; A61K 38/16; A61K 35/14; C07B 47/00
[52] U.S. Cl. ............................. 435/70.1; 514/6; 540/145; 530/385
[58] Field of Search .................................. 435/71.1, 171, 435/337, 421, 70.1, 70.3; 530/385, 380; 540/145; 514/6; 424/9.61

[56] References Cited

PUBLICATIONS

Siefermann–Harms et al. "Reassembly of solubilized chlorophyll–protein complexes in proteolipid particles–comparison of monogalactosyldiacylgyl and two phospholipids", Biochim. Biophys. Acta (1987) 892: 303–313.

Brady et al. General Chemistry, 2nd. edition. (Wiley: New York) (1978) pp. 362–363.

Antonini et al. "Studies on the structure of hemoglobin III. Physicochemical properties of reconstituted hemoglobins", Biochim. Biophys. Acta (1964) vol. 79, pp. 284–292.

Tavill et al. "The role of heme in the synthesis and assembly of hemoglobin", J. Biol. Chem. (1968) vol. 243(19), pp. 4987–4999.

Kephart, "Chlorophyll Derivatives—Their Chemistry, Commercial Preparation and Uses", Economic Botany pp. 3–38. vol. 9 (1955).

Dougherty et al. "Journal of the American Chemical Society", vol. 88, No. 21, (1966) pp. 5307–5308.

Smith et al., "New Efficient Total Syntheses of Derivatives of Protoporphyrin–1X", Journal of Heterocyclic Chemistry, vol. 20, No. 5, (1983) pp. 1383–1388.

Smith et al., "Syntheses of Isomers of Protoporphyrin–1X: With Permuted Propionic Side–Chains" Journal of Heterocyclic Chemistry, vol. 22, No. 4, (1985) pp. 1041–1044.

Fanelli et al., "Studies on the Structure of Hemoglobin: Physicochemical Properties of Human Globin" Biochemica Biophysica Acta, vol. 30, No. 3, (1958) pp. 608–615.

*Primary Examiner*—Jean C. Witz
*Assistant Examiner*—Susan Hanley
*Attorney, Agent, or Firm*—Foley & Lardner

[57] ABSTRACT

Hemin-like porphyrins can be prepared from chlorophylls which may be used as intermediates to form functionally active hemoproteins. The porphyrins can be reacted with apoproteins in vitro or added to a cell culture and combined intracellularly with apoproteins to form functionally active hemoproteins.

30 Claims, No Drawings

PREPARATION OF HEMOPROTEINS FROM APOPROTEINS AND HEME-LIKE PORPHYRINS DERIVED FROM CHLOROPHYLL

BACKGROUND OF THE INVENTION

Hemoproteins are connected intrinsically with many key cellular processes such as reversible oxygen binding, oxygen storage, peroxide destruction, and electron transfer reactions. They contain two types of components: metal-containing porphyrins and apoproteins. The combination of these two components, when properly configured, provides functionally-active porphyroproteins (e.g., hemoglobin).

A variety of medical and commercial processes require large amounts of specific porphyroproteins for uses such as blood replacement, food modification, biochemical reactions, and the like. Historically, these needs have been met by the isolation and purification of naturally-occurring porphyroproteins, but these sources increasingly are coming back under attack because they can harbor infectious particles, including prions, and because they can cause antigenic reactions in people due to species' differences in the proteins.

Recently, efforts have been directed toward avoiding some of these problems by producing species-specific apoproteins (e.g., human-type globin) in fermentation/incubation and modified-animal systems using genetically-modified cells. Such procedures can provide species-specific apoproteins, and fermentation/incubation procedures can also provide apoproteins (proteins without their associated co-factors) free of animal-derived infectious particles.

One approach to manufacturing hemoglobin involves adding hemin (a porphyrin) to globin (an apoprotein) isolated from a natural source (such as blood), which combine, under appropriate conditions, with each other to form hemoglobin in vitro. A variation of this approach involves adding hemin to a culture/fermentation medium containing bacterial or yeast cells which have been genetically engineered to produce globin in the cell. In this latter in vivo method, the host cell takes up the hemin which has been added to the culture/fermentation medium and combines the hemin in vivo with the globin. The resulting hemoglobin can be removed from the host cell using conventional cell lysis techniques. However, in these methods, the porphyrin portion of the haloproteins must still be produced by isolation from natural sources such as animal blood.

There are at least four major problems associated with such isolation procedures from natural sources:

1. There is a serious concern about infectious particles, including prions and prion fragments, being present. This is a major ethical and liability concern.
2. There is a relatively high cost of extracting porphyrins from natural sources.
3. There are serious religious prohibitions in many groups whose rules proscribe products either from certain kinds of animals, from animals of any kind, or from animal blood.
4. There are major governmental regulatory problems regarding natural animal products.

The concern about infectious particles can be met partially by subjecting the porphyrins to very harsh acid and high temperature conditions that are known to degrade various microorganisms and viruses. However, recent research on prions ("infectious protein molecules") has shown that it is not possible to know for sure how much degradation is necessary to lose such "infectiousness". And, even if infectivity is not a problem, there still remain problems of high cost, sources of origin and governmental regulations.

SUMMARY OF THE INVENTION

The present inventor discovered that genetically-modified or unmodified cells, organelles, organisms, and the like, can take up non-hemin porphyrins and metalloporphyrins (or alternatively hereafter "porphyrins") from fermentation/incubation media to form porphyroproteins in vivo, i.e., within the cell, that have comparable functional activity to the corresponding naturally-occurring porphyroproteins. The cells can then be lysed by conventional means to obtain the desired porphyroproteins.

Moreover, the present inventor discovered that such non-hemin porphyrins can form porphyroproteins that have comparable functional activity to naturally-occurring porphyroproteins when they are combined in vitro with apoproteins produced by genetically-modified cells and organisms. Apoproteins isolated from genetically-engineered cells or organisms can be mixed with the non-hemin porphyrins and metalloporphyrins to form porphyroproteins in vitro, under appropriate conditions, having comparable functional activity to naturally occurring porphyroproteins.

Additionally, the present inventor discovered that chlorophyll, chlorophyll-like and chlorophyll-derived compounds, when appropriately treated by chemical means, can provide hemin and hemin-like porphyrin and metalloporphyrin compounds useful in the above-mentioned discoveries, but with much lower costs and with the advantage of being derived from plant (rather than animal) sources, without any risk of animal-derived infectious particles, and without many of the governmental regulation problems.

DETAILED DESCRIPTION OF THE PREFERRED EMBODIMENTS

The porphyrins of the present invention are preferably derived from chlorophylls and chlorophyll-like compounds (hereafter "chlorophylls"), which are represented by the following formula I:

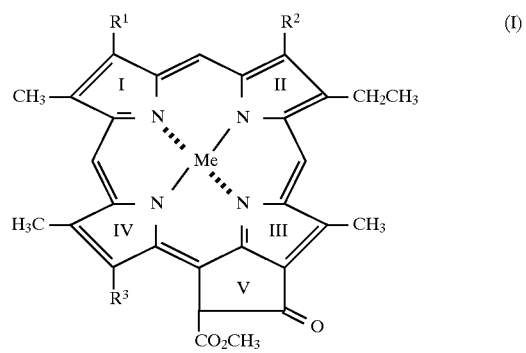

wherein the pyrrole ring II may optionally be reduced;
$R^1$ represents vinyl, formyl, or hydrogen;
$R^2$ represents methyl, methanal, or hydrogen; and
$R^3$ represents —$(CH_2)_2COOH$, or —$(CH_2)_2COO$-phytyl;
or wherein structure (I) is chlorophyll c as taught by Dougherty, et al., J. Am. Chem. Soc., vol. 88, page 5037 (1966), the text of which is incorporated by reference herein.

Preferred chlorophylls are chlorophylls a, b, c, and d, chlorophyllides a, b, c, and d, chlorophyllins a, b, c, and d, and bacterio-chlorophylls.

Preferred sources of the chlorophylls used in the present invention are higher plants and grasses, bacteria, algae, seaweeds, kelps and other photosynthetic cells/organisms.

Appropriate sequential chemical treatments can open the cyclopentanone ring of the chlorophyll molecule and provide a wide variety of heme-like porphyrin analogues. For example, the cyclopentanone ring can be opened with gentle alkaline hydrolysis which simultaneously saponifies the methyl and phytyl esters. The magnesium atom can then be replaced with an iron atom to yield iron chlorophyllins, or the chlorophyllin porphyrins can be modified chemically to yield a variety of heme-like porphyrins. Alternatively, oil soluble chlorophylls can be treated with acid to yield pheophytin, which can be further modified to yield a wide variety of porphyrins, including pyrroporphyrin and mesoporphyrin. The literature describing such conversions and modifications include Hans Fischer's work in the 1900's. A good review of the chemistry is provided in Kephart, *Econ. Bot.*, vol. 9, pages 3–38 (1955), which is incorporated by reference herein.

Iron, manganese, copper, magnesium, or other metals can be inserted into the porphyrin, if so desired. In order to be functionally active, porphyroproteins must contain metals.

The porphyrins of the present invention have the following structural formulae:

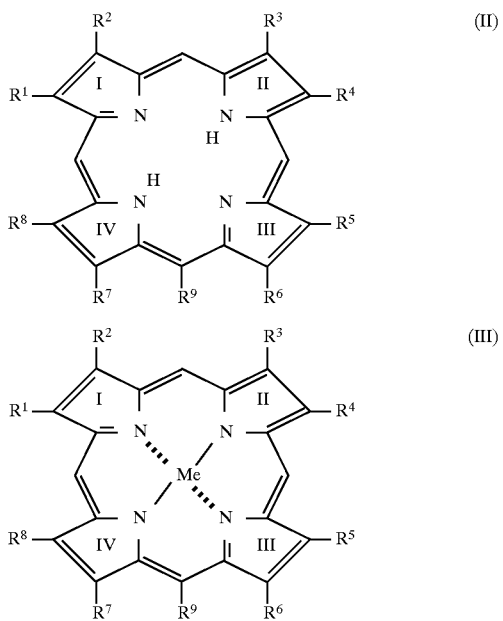

wherein Me represents a metal ion; $R^1$ through $R^9$ independently represent hydrogen, methyl, ethyl, vinyl, propyl, hydroxymethyl, hydroxyethyl, hydroxypropyl, formyl, ethanalyl or propionalyl groups.

When porphyroproteins are produced using the above porphyrins, the metal atom (Me in the above formula III) can be introduced either before or after the porphyrins are combined with an apoprotein, and either inside or outside the cell, depending on the production method selected.

The porphyrins of the above formulae II and III are preferably derived from the chlorophylls of formula I, although the non-hemin porphyrins of formulae II and III can be derived from hemin and other non-chlorophyll porphyrins using known chemical techniques for modifying the substituents of porphyrins. Hemin itself is represented in the above formula III wherein $R^6=R^7$=propionyl, $R^1=R^3=R^5=R^8$=methyl, $R^2=R^4$=vinyl, and $R^9$=hydrogen.

Preferred porphyrins are hemin, deuteroheme, mesoheme, hematoheme, etioheme, rhodoheme, protoheme, phylloheme, coproheme, iron chlorophyllin, dibromoprotoheme, isoheme, hemin C, pyrroheme, siroheme, their non-metal-containing counterparts, and the methyl, ethyl, propyl, formyl, acetyl, cysteine, and proprionyl derivatives thereof.

The types of chemical reactions used to replace, delete and modify hemin and other porphyrin side chains (substituents) include all of the usual synthetic organic reactions normally used in organic syntheses. As noted above, the literature in this area dates back to Hans Fischer. A good review is provided in Sambrotta, et al., *Tetrahedron*, vol. 45, page 6645 (1989) and the references cited therein; Smith et al., *J. Heterocycl. Chem.*, vol. 20, page 1383 (1983); and *id.*, vol. 22, page 1041 (1985); all of which are incorporated by reference herein.

The porphyrins of the present invention are preferably prepared in water-miscible or water-soluble systems so as to be available for uptake into cells, organelles and organisms, or so that they can react with aqueous-based apoproteins in vitro. To this end, the porphyrins and metalloporphyrins can be dissolved or suspended in aqueous solutions, or in water-miscible solvents like alcohols, glycols, dimethyl sulfoxide, dimethylformamide, formamide, and the like.

Alternatively, the porphyrins and metalloporphyrins can be dissolved or suspended in lipophilic materials like oils, and then micro-emulsified with aqueous solutions or with water-miscible solvents. Finally, the porphyrins and metalloporphyrins can be dispersed and coated in a micelle-system (e.g., a lipid bilayer system), and then further dispersed in an aqueous solution or in a water miscible solvent. The emulsified and micelle-forms of the porphyrins and metalloporphyrins can be useful in some systems by providing for slow release, and/or enhanced phagocytosis.

There are two main routes by which the porphyrins of the present invention can be combined with apoproteins to form functionally-active porphyroproteins. In one embodiment, living cells, groups of cells, or organelles take up the porphyrins and metalloporphyrins from the fermentation/incubation media. These compounds can then be combined inside the cell directly, as is, with the apoproteins, or they can be modified inside the cell before the actual combination occurs with the apoprotein, depending on the kind of intracellular reactions taking place inside the particular cell being used or depending on the extracellular chemical reactions employed prior to uptake by the cell.

Depending on the kind of cell and extracellular chemical reactions employed, such pre-combination modifications include additions, deletions, esterification and/or modifications of the porphyrin side chains $R^1$ through $R^9$, and/or the addition, deletion, or substitution of a central metal atom in the porphyrin structure itself. In this latter modification, the most common final product is one containing an iron atom to form a heme-like compound.

Various systems are known in the art in which free-living cells, groups of cells, and organelles are maintained and grown under artificial conditions using a variety of fermentation/incubation media and systems, ranging from the use of a fermentor to the use of a plant or animal host (e.g., ascites cells). Such systems have included a wide variety of cells ranging from bacteria, yeast, other fungi, algae, seaweeds, kelps, other plant cells, protozoans, metazoans, other animal cells, groups or clusters of plant or animal cells, hybridoma cells, and various combinations thereof. Further, these cells can either be the naturally-occurring cells producing their normal porphyroproteins, or increasingly, these cells are genetically-modified so as to produce apoproteins not normally found in these cells.

Preferred cells for producing the apoproteins of the present invention are bacterial cells, particularly *E. coli*, yeast cells, particularly *S. cerevisiae*, alga cells, rat and mouse hybridoma cells, and animal tumor cells. There also are many examples wherein a hemoprotein is the specifically sought after end product being produced in genetically modified cells. In these instances, hemin-like porphyrins are supplied directly to the fermentation/incubation media, in either sterilized or non-sterile form, during the production stage.

The second process by which porphyrins and metalloporphyrins are combined with apoproteins to form functionally-active proteins is an extracellular process wherein the porphyrins are added to aqueous solutions of apoprotein to form functionally-active porphyroproteins, particularly those having hemin-like porphyrins. The actual coupling (combining) of these porphyrins with the apoproteins, for example, can be measured quantitatively with high precision using a spectrophotometer, using a wave-length appropriate for the particular non-hemin porphyrin being coupled.

As an example of this in vivo recombination, protoheme (protohemin, hemin) can be shown to combine stoichiometrically with apoglobin at pH 7.1 (4 molecules hemin per molecule of apoglobin) to form hemoglobin that is identical to natural hemoglobin in all measurable properties including absorption spectra, ultracentrifuge sedimentation patterns, electrophoretic mobility, stability to temperature and pH extremes, and reaction kinetics with oxygen.

When various metalloporphyrin compounds are substituted for hemin in coupling reactions with various apoproteins, they combine in a similar manner to hemin and form functionally-active metalloporphyroproteins with almost identical properties to the natural hemin-protein. The differences between the compounds themselves, and between themselves and hemin, seem to be subtle differences not appreciably affecting functionality. For example, with globin as the apoprotein, meso-, deutero-, etio- and hematohemes have a slightly lower affinities for the globin as compared to hemin, as determined by the fact that hemin will preferentially displace these hemin-type porphyrins from the apoprotein. However, the oxygen-carrying properties of these unnatural hemoglobins are similar to that of hemoglobin itself. Similarly, stable unnatural hemoproteins have been formed from heme-type compounds which structurally are considerably different from hemin, including the dialkyl esters of proto-, meso-, etio-, deutero-, and hematohemes. These unnatural hemoproteins also were found to have similar physiological functions to the natural hemoproteins. As before, the differences from natural hemoglobin were subtle ones, in these cases, having to do with the so-called "cooperative behavior" of hemoglobin molecules.

Similar functional activities are found to result for hemoglobins, myoglobins, chlorophylls, catalases, peroxidases, cytochromes, tryptophane pyrrolases, and cytochrome P-450's when the appropriate apoproteins are combined with a wide variety of porphyrin and metalloporphyrin compounds like deuteroheme, mesoheme, hematoheme, etioheme, rhodoheme, protoheme, phylloheme, coproheme, iron chlorophyllin, dibromoprotoheme, isoheme, hemin C, pyrroheme, siroheme, as well as the non-metal-containing porphyrin-counterparts to these heme compounds, and with the methyl, ethyl, propyl, formyl, acetyl, cysteine and proprionyl derivatives of these heme and corresponding non-metal-containing porphyrin compounds.

Finally, it should be noted that in all cases tested, the non-metal-containing porphyrin analogues of the heme-type compounds also seemed to bind in a similar way to the apoproteins as did their heme counterparts. However, the functionality of these porphyroproteins could not be demonstrated because porphyroproteins are inactive due to the absence of the metal atom (in these cases, iron). This is not a problem, however, as metal atoms can be introduced into such porphyrin molecules either before or after they are combined with the apoprotein.

Under normal circumstances, iron is found in the hemoglobins, myoglobins and catalases; iron and manganese are active in peroxidases; copper is required by cytochromes; and magnesium is found in chlorophylls.

The present invention is further illustrated by, though in no way limited to, the following examples.

EXAMPLE 1

Protoheme (hemin) is dissolved in 0.1M phosphate buffer, pH 7.0. It then is deoxygenated under vacuum and reduced with sodium dithionite. The apoglobin, isolated from genetically-modified *E. coli* cells, is prepared by the method of Rossi-Fanelli et al., (*Biochim. Biophys. Acta* vol. 30, page 608, 1958), which is incorporated by reference herein, suspended in cold 0.1M phosphate buffer, pH 7.0, and used as soon as possible. The reduced hemin is added slowly, with mixing, to the freshly prepared apoglobin solution at 4° C. The coupling is followed spectrophotometrically at 405 nm. Excess heme is removed in a Bio-Gel P-2 column, and the reconstituted hemoglobin is evaluated against natural hemoglobin. There are no differences as regards absorption spectra, ultracentrifuge sedimentation patterns, electrophoretic mobility, stability to temperature and pH extremes, and reaction kinetics with oxygen.

EXAMPLE 2

Pyrrohemin was prepared from pyrroporphyrin, which in turn was prepared from chlorophyll a:

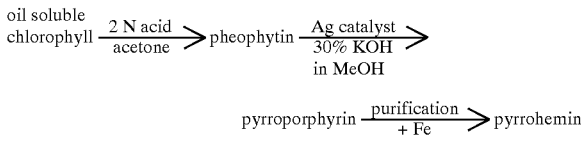

Pyrrohemin is suspended in 0.1N NaOH and slowly introduced into a fermentation broth containing a genetically-modified strain of *E. coli* capable of forming a modified human-type apoglobin. After an appropriate incubation time, the *E. coli* cells are collected and the pyrrohemoglobin is isolated and purified. The final recombinant pyrrohemoglobin is evaluated against both in vitro-produced pyrrohemoglobin and natural hemoglobin. All three preparations are essentially identical as regards the evaluations reported in Example 1.

While the invention has been described in detail and with reference to specific embodiments thereof, it will be apparent to one skilled in the art that various changes and modifications can be made therein without departing from the spirit and scope of the invention.

What is claimed is:

1. A method of producing a hemoprotein comprising an apoprotein and a heme-like porphyrin wherein said heme porphyrin is represented by structure II or III:

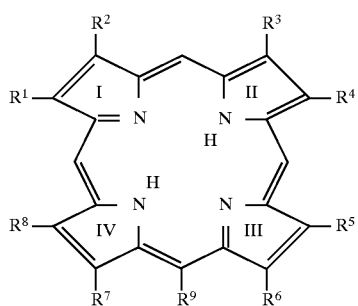

or

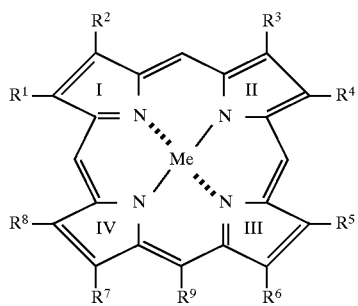

wherein R¹ through R⁹ independently represent hydrogen, methyl, ethyl, vinyl, propyl, hydroxymethyl, hydroxyethyl, hydroxypropyl, formyl, ethanalyl or propionalyl and Me is a metal atom; wherein said heme-like porphyrin is obtained from chlorophyll; comprising the steps of a) contacting a composition comprising said heme-like porphyrin and a carrier with a fermentation or incubation medium containing naturally-occurring cells, genetically modified cells, organelles, organisms or combinations thereof, which produce an apoprotein; and b) collecting the hemoprotein produced in step a).

2. A method of producing a hemoprotein comprising an apoprotein and a heme-like porphyrin wherein said heme porphyrin is represented by structure II or III:

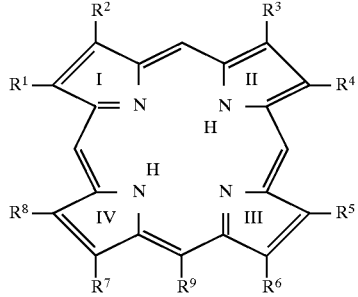

or

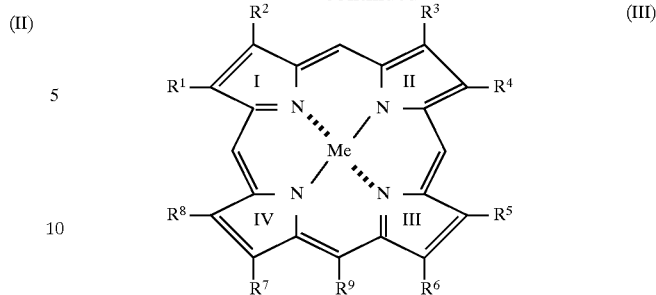

wherein $R^1$ through $R^9$ independently represent hydrogen, methyl, ethyl, vinyl, propyl, hydroxymethyl, hydroxyethyl, hydroxypropyl, formyl, ethanalyl or propionalyl and Me is a metal atom; wherein said heme-like porphyrin is obtained from chlorophyll; comprising the steps of a) contacting a composition comprising said heme-like porphyrin and a carrier with a medium containing an apoprotein; and b) collecting the hemoprotein produced in step a).

3. A method as claimed in claim 1 wherein said heme-like porphyrin is selected from the group consisting of hemin, deuteroheme, mesoheme, hematoheme, etioheme, rhodoheme, protoheme, phylloheme, coproheme, iron chlorophyllin, dibromoprotoheme, isoheme, hemin C, pyrroheme, siroheme, their non-metal-containing counterparts, and the methyl, ethyl, propyl, formyl, acetyl, cysteine, and proprionyl derivatives thereof.

4. A method as claimed in claim 2 wherein said heme-like porphyrin is selected from the group consisting of hemin, deuteroheme, mesoheme, hematoheme, etioheme, rhodoheme, protoheme, phylloheme, coproheme, iron chlorophyllin, dibromoprotoheme, isoheme, hemin C, pyrroheme, siroheme, their non-metal-containing counterparts, and the methyl, ethyl, propyl, formyl, acetyl, cysteine, and proprionyl derivatives thereof.

5. A method as claimed in claim 1 wherein the apoprotein is selected from the group consisting of the apoprotein for hemoglobin, myoglobin, catalase, peroxidase, cytochrome, tryptophane pyrrolase, and cytochrome P-450.

6. A method as claimed in claim 2 wherein the apoprotein is selected from the group consisting of the apoprotein for hemoglobin, myoglobin, catalase, peroxidase, cytochrome, tryptophane pyrrolase, and cytochrome P-450.

7. A method as claimed in claim 1 wherein the cells, organelles, and organisms are selected from the group consisting of bacteria, yeast, fungi, algae, plants, plant cells, protozoans, metazoans, animals, and animal cells.

8. A method as claimed in claim 1, wherein the porphyrin is represented by structure II and the process further comprises the step of adding a metal ion to the hemoprotein of step b.

9. A method as claimed in claim 2, wherein the porphyrin is represented by structure II and the process further comprises the step of adding a metal ion to the hemoprotein of step b.

10. The method as claimed in 1, wherein said heme-like porphyrin is produced by opening the cyclopentanone ring of a chlorophyll.

11. The method as claimed in claim 10, wherein the step of opening the cyclopentanone ring of the chlorophyll is effected by alkaline hydrolysis.

12. The method as claimed in claim 11, wherein the chlorophyll is represented by structure I:

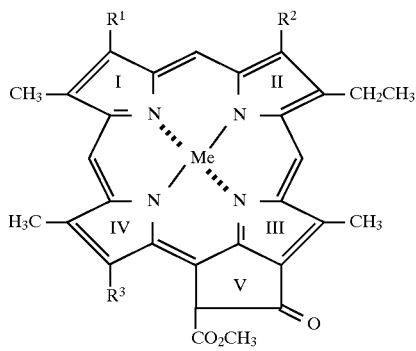

(I)

wherein the pyrrole ring II of structure I may be reduced;
$R^1$ represents vinyl, formyl, or hydrogen;
$R^2$ represents methyl, formyl, or hydrogen;
$R^3$ represents $—(CH_2)_2COOH$, or $—(CH_2)_2COO$-phytyl;
or the chlorophyll is chlorophyll c.

13. The method as claimed in claim 12, wherein the heme-like porphyrin is pyrrohemin obtained from chlorophyll a.

14. The method as claimed in 2, wherein said heme-like porphyrin is produced by opening the cyclopentanone ring of a chlorophyll.

15. The method as claimed in claim 14, wherein the step of opening the cyclopentanone ring of the chlorophyll is effected by alkaline hydrolysis.

16. The method as claimed in claim 15, wherein the chlorophyll is a represented by structure I:

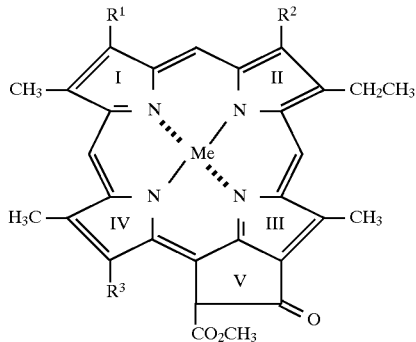

(I)

wherein the pyrrole ring II of structure I may be reduced;
$R^1$ represents vinyl, formyl, or hydrogen;
$R^2$ represents methyl, formyl, or hydrogen;
$R^3$ represents $—(CH^2)_2COOH$, or $—(CH_2)_2COO$-phytyl;
or the chlorophyll is chlorophyll c.

17. The method as claimed in claim 16, wherein the heme-like porphyrin is pyrrohemin obtained from chlorophyll a.

18. A method for producing a hemoprotein comprising the steps of
   a) opening the cyclopentanone ring of a chlorophyll to obtain a heme-like porphyrin;
   b) contacting the heme-like porphyrin of step a) and a carrier with an apoprotein; and
   c) collecting the hemoprotein produced in step b).

19. The method as claimed in claim 18, wherein the step of opening the cyclopentanone ring of the chlorophyll is effected by alkaline hydrolysis.

20. The method as claimed in claim 19, wherein the chlorophyll is represented by structure I:

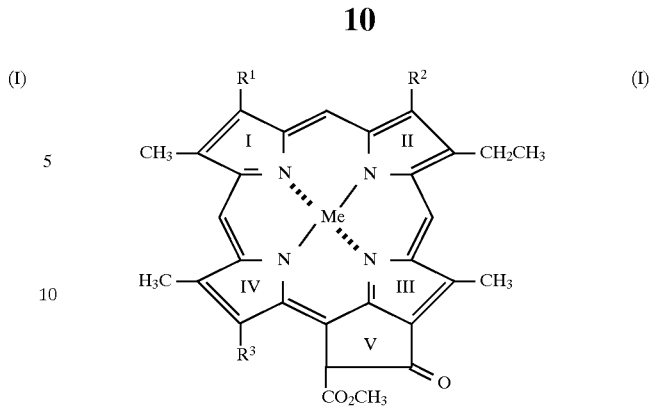

(I)

wherein the pyrrole ring II of structure I may be reduced;
$R^1$ represents vinyl, formyl, or hydrogen;
$R^2$ represents methyl, formyl, or hydrogen;
$R^3$ represents $—(CH_2)_2COOH$, or $—(CH_2)_2COO$-phytyl;
or the chlorophyll is chlorophyll c.

21. The method as claimed in claim 20, wherein the heme-like porphyrin is pyrrohemin obtained from chlorophyll a.

22. A method for producing a hemoprotein comprising the steps of
   a) opening the cyclopentanone ring of a chlorophyll to obtain a heme-like porphyrin;
   b) contacting the heme-like porphyrin of step a) and a carrier with a fermentation or incubation medium containing naturally-occurring cells, genetically modified cells, organelles, organisms or combinations thereof;
   c) collecting the hemoprotein produced in step b).

23. The method as claimed in claim 22, wherein the step of opening the cyclopentanone ring of the chlorophyll is effected by alkaline hydrolysis.

24. The method as claimed in claim 23, wherein the chlorophyll is represented by structure I:

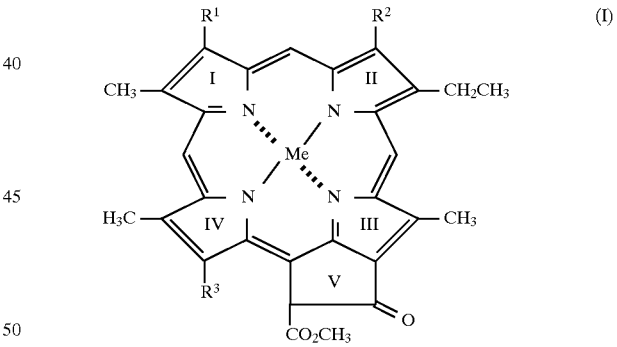

(I)

wherein the pyrrole ring II of structure I may be reduced;
$R^1$ represents vinyl, formyl, or hydrogen;
$R^2$ represents methyl, formlyl, or hydrogen;
$R^3$ represents $—(CH_2)_2COOH$, or $—(CH_2)_2COO$-phytyl;
or the chlorophyll is chlorophyll c.

25. The method as claimed in claim 24, wherein the heme-like porphyrin is pyrrohemin obtained from chlorophyll a.

26. A method for producing a hemoprotein, comprising the steps of
   a) extracting a porphyrin from photosynthetic cells,
   b) converting said porphyrin of step a) into a heme-like porphyrin;
   (c) either
      (i) contacting the heme-like porphyrin of step b) and a carrier with a fermentation or incubation medium containing naturally-occurring cells, genetically modified cells, organelles, organisms or combinations thereof; or
  (ii) contacting the heme-like porphyrin of step b) and a carrier with an apoprotein; and d) collecting the hemoprotein produced in step c).

27. The method of claim 26 wherein the porphyrin of step a) is selected from the group consisting of a chlorophyll and a plant-produced porphyrin.

28. The method of claim 27, wherein the plant-produced porphyrin is protoporphyrin IX.

29. The method of claim 26, wherein said porphyrin of step a) is a metalloporphyrin.

30. The method of claim 29, wherein the hemeprotein of step a) is hemoglobin.

* * * * *